United States Patent [19]

Romiti

[11] Patent Number: 6,084,129

[45] Date of Patent: Jul. 4, 2000

[54] PROCESS FOR REDUCING THE RESIDUAL FREE AMMONIA EMISSIONS FROM AN UREA PRODUCTION PLANT

[75] Inventor: Domenico Romiti, Lugano, Switzerland

[73] Assignee: Urea Casale S.A., Lugano-Besso, Switzerland

[21] Appl. No.: 09/104,355

[22] Filed: Jun. 25, 1998

[30] Foreign Application Priority Data

Jun. 26, 1997 [EP] European Pat. Off. .............. 97201956

[51] Int. Cl.$^7$ .................................................. C07C 273/16
[52] U.S. Cl. .................... 564/73; 564/3; 564/67; 504/327
[58] Field of Search .................. 564/3, 67, 73; 504/327

[56] References Cited

U.S. PATENT DOCUMENTS

| | | |
|---|---|---|
| 4,001,320 | 1/1977 | Kassenbrood ........................ 260/555 A |
| 4,308,234 | 12/1981 | Pastormerlo ............................. 422/193 |
| 4,320,103 | 3/1982 | Pagani ..................................... 423/359 |
| 5,527,961 | 6/1996 | Granelli et al. ........................... 564/73 |

*Primary Examiner*—Shailendra Kumar
*Attorney, Agent, or Firm*—Sughrue, Mion, Zinn, Macpeak & Seas, PLLC

[57] ABSTRACT

A process for reducing the residual free ammonia emissions from an urea production plant comprises the step of feeding a gas flow comprising carbon dioxide (8) to a melt urea flow (3) coming from the concentration section (13) of the plant.

8 Claims, 1 Drawing Sheet

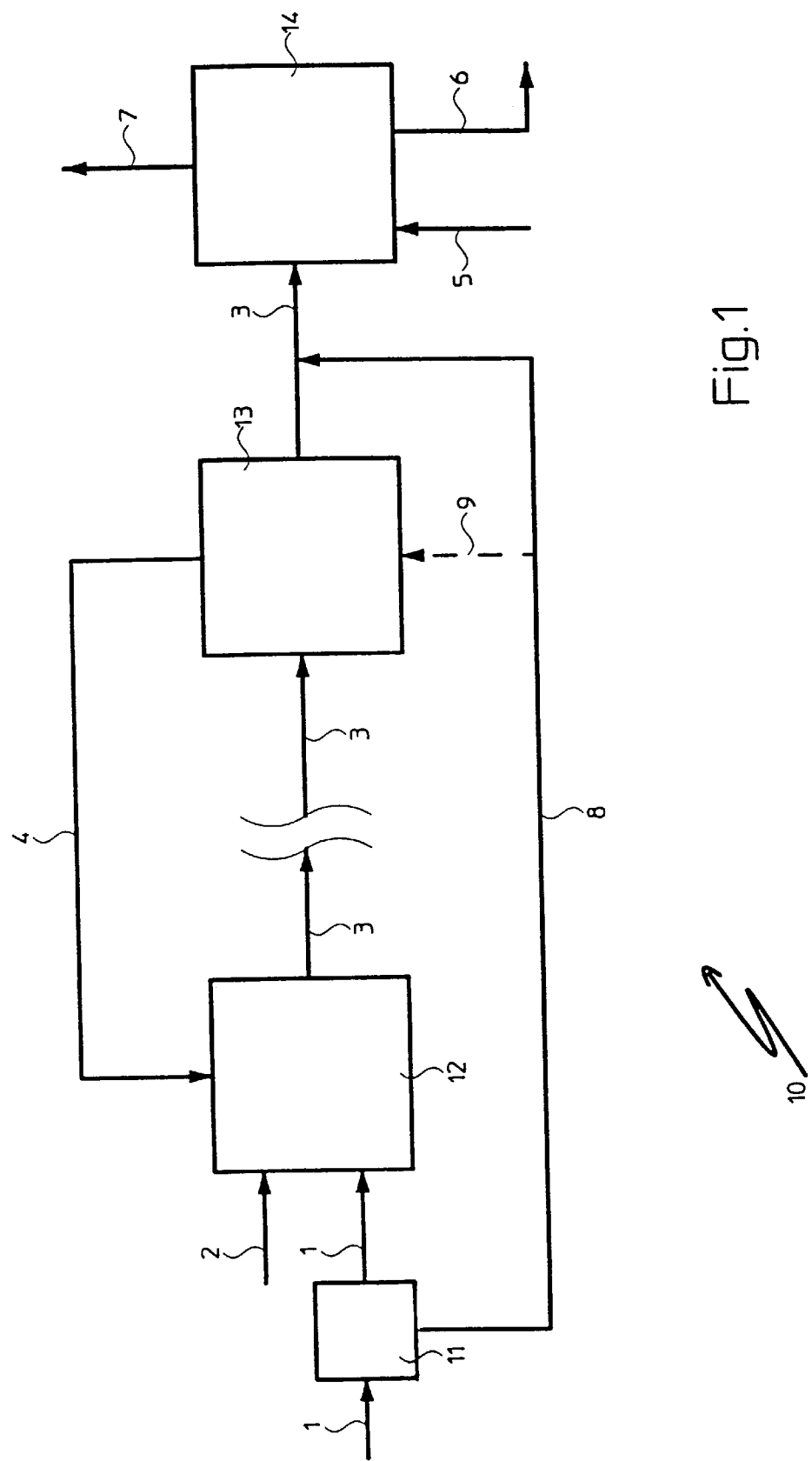

PROCESS FOR REDUCING THE RESIDUAL FREE AMMONIA EMISSIONS FROM AN UREA PRODUCTION PLANT

DESCRIPTION

1. Field of application

The present invention relates to a process for reducing the residual free ammonia emissions from an urea production plants comprising a urea synthesis section and a urea concentration section.

The invention also relates to a plant for implementation of the above mentioned process, as well as to a method for the modernisation of a urea production plant.

As known, in the field of industrial urea production there is increasingly felt the need to provide a process allowing to substantially reduce the emissions of residual free ammonia released by urea production plants, in order to comply with the increasingly strict norms against pollution in force in industrialised countries.

In fact, even though urea production plants are equipped with special treatment sections, melt urea obtained following the concentration step of the urea solution produced in the synthesis section, always and anyway contains some residual free ammonia that escapes from the production plant and disperses in the air as a polluting agent.

This is due to the fact that it is not possible—unless to very high energy and operating costs that cannot be met to separate from the produced urea all the unreacted ammonia leaving the synthesis section (ammonia together with carbon dioxide is a reagent for urea synthesis).

Moreover, the same urea tends spontaneously to decompose into biuret and ammonia according to the following reaction:

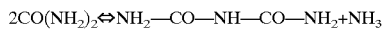

$$2CO(NH_2)_2 \Leftrightarrow NH_2\text{—}CO\text{—}NH\text{—}CO\text{—}NH_2 + NH_3$$

As a consequence, also the more concentrated melt urea enriches in ammonia before it can be solidified in the special prilling or granulation section, and said ammonia adds to the previously non separated ammonia and escapes unavoidably from the urea production plant.

2. Prior art

In order to met the above requirement, there has been proposed in the field a process to reduce residual free ammonia emissions from a urea production plant, comprising the step of adding to the melt urea resulting from the concentration section a given amount of an inorganic acid, preferably a sulphuric or a phosphoric acid.

By so doing, at least a part of the free ammonia comprised in melt urea gets in touch with the acid and reacts forming the respective salt, for instance ammonium sulphate or ammonium phosphate, which solidify together with urea.

This process has been described in U.S. Pat. No. 5,527,961.

However, to achieve this aim, the above described process shows several drawbacks, the first of which is that the addition of an inorganic acid—even if in small amounts involves non negligible problems of corrosion of the apparatuses that get in touch with such acid and thus oblige the user to carry out frequent and expensive operations of plant control and maintenance.

Besides, to implement the above described process, the plant must be in any case provided with an additional acid feeding line that involves several storing, dosing and regulation devices whose cost would not be negligible as would not be negligible the cost of the substance added to melt urea.

Hence, the implementation of the process according to the prior art is rather complex from the technical point of view and involves relatively high investment, maintenance and operating costs.

A further drawback of this process ensues from the fact that, once solidified, urea has such a content of ammonium salts that it becomes unfit for industrial utilisation. Moreover, the presence of sulphur and nitrogen in solid urea may cause the pollution of the soil where such urea is dissolved, for instance the pollution of a water bed.

Because of these drawbacks, the above process was seldom applied till now, in spite of the increasingly felt requirement in the field.

SUMMARY OF THE INVENTION

The problem underlying the present invention is to make available a process to reduce residual free ammonia emissions from an urea production plant, of simple implementation, low operating, investment and maintenance costs, and such as to supply a final product having a high fertilising potential.

The above mentioned problem is solved, according to the invention, by a process of the above mentioned type, characterised in that it comprises the following step:

feeding a gas flow comprising carbon dioxide to a melt urea flow coming from said urea concentration section.

In the following of the description and subsequent claims, with the term: gas flow comprising carbon dioxide, it is intended to mean a gas flow comprising carbon dioxide and other inert gases that are present in low concentrations, such as for instance nitrogen, hydrogen, oxygen, air or carbon monoxide, or preferably comprising only carbon dioxide.

Thanks to the process according to the present invention, it is possible to obtain, in an extremely simple, effective and economic way, a substantial, or even complete, reduction in ammonia emissions released by a urea production plant, obtaining at the same time a high yield final product (fertiliser).

In fact, the carbon dioxide fed to the melt urea flow coming from the concentration section, advantageously reacts with the ammonia contained in urea forming carbamate and/or carbonate/bicarbonate, i.e. non polluting fertilising compounds, very similar to urea.

As a consequence, besides actively neutralising the residual free ammonia still present in melt urea, preventing in this way polluting agents from being released by the production plant, the process according to the present invention provides a final product having a high effectiveness as a fertiliser.

Moreover, since carbamate and/or carbonate/bicarbonate obtained from the reaction of carbon dioxide with the free ammonia still present in melt urea have chemical-physical properties that are very similar to those of urea, the product obtained thanks to the present process is advantageously useful also for industrial uses.

A non negligible advantage of the process according to the invention is also provided by the fact that, as the reaction between carbon dioxide and ammonia is a reaction of the exothermic type, the heat released by said reaction can be advantageously exploited to keep urea at the melt state between the concentration section and the solidification section (prilling or granulation section) of the plant. In this way it is possible to reduce the amount of steam conventionally utilised to indirectly heat the melt urea flow, providing therefore savings in terms of steam and energy consumption.

Advantageously, the implementation of the present process does not involve high investment, operating or maintenance costs, as carbon dioxide, besides being an extremely economical substance, does not need special treatments or operating conditions, and further, being completely non corrosive, it does not affect plant apparatuses adversely. No additional devices are therefore needed for storing, dosing and regulating the gas flow comprising carbon dioxide.

According to an alternative embodiment of the invention, the present process advantageously provides the further step of feeding a gas flow comprising carbon dioxide to the urea concentration section.

In this way, there is facilitated the recovery of free ammonia present in the urea solution sent to the concentration section, causing the same to react with carbon dioxide.

Thanks to this additional feeding step, a reduction is obtained in the free ammonia to be separated and recycled as such to the synthesis section, correspondingly reducing therefore the amount of recycle water as well as the energy consumption of the concentration section.

Particularly advantageous results have been achieved by feeding to the flow of melt urea an amount of carbon dioxide comprised between 85 and 850 grCO$_2$/tonUREA.

Actually, it has been found that by operating within said parameters it is possible to neutralise almost all of the free ammonia comprised in melt urea.

In any case, the amount of carbon dioxide to be added to melt urea is not particularly critical; quite the contrary, considering the low cost of this substance, it may be advantageous to operate with excess carbon dioxide, facilitating in this way the complete neutralisation of residual free ammonia.

This possibility of operating in extremely flexible conditions markedly contrasts with the aforementioned process of the prior art, where it is necessary to perform a careful and precise dosing of the amount of acid to be sent to the melt urea flow, to keep down as much as possible the damages ensuing from the corrosion of the apparatuses.

According to a preferred embodiment of the invention, the present process advantageously provides a step of taking the gas flow comprising carbon dioxide from a gas flow comprising carbon dioxide feeding the urea synthesis section.

This is possible by the fact that carbon dioxide is a component present in large amounts in the production plant, being a reagent for urea synthesis.

As a consequence, by advantageously exploiting the raw materials and the apparatuses already existing in the plant, the above mentioned problem may be solved in an extremely simple and reliable way, to quite negligible costs of investment, operating and maintenance of the plant intended for the implementation of the present process.

For the implementation of said process, the present invention advantageously provides a urea production plant comprising a urea synthesis section and a urea concentration section, characterised in that it further includes means for feeding a gas flow comprising carbon dioxide to the melt urea flow coming from said concentration section.

According to a further aspect of the invention, a method is also provided for the in-situ modernisation of a urea production plant comprising a urea synthesis section and a urea concentration section, said method comprising the step of:

providing means for feeding a gas flow comprising carbon dioxide to a melt urea flow coming from said concentration section.

Thanks to said modernisation method of an existing urea production plant, it is possible to obtain a process that can reduce the emissions of residual free ammonia released by the plant, in a simple and reliable way and to low investment, operating and maintenance costs.

The characteristics and advantages of the inventions are set forth in the description of an embodiment thereof given below by way of non-limiting example with reference to the attached drawing.

SHORT DESCRIPTION OF THE DRAWING

FIG. 1 shows a block diagram of the process for reducing the residual free ammonia emissions from an urea production plant, according to a preferred embodiment of the invention.

DETAILED DESCRIPTION OF A PREFERRED EMBODIMENT

With reference to FIG. 1, there is generally indicated by 10 a block diagram which shows schematically the steps of the process for reducing the residual free ammonia emissions from an urea production plant.

As will be seen later on, such process can reduce the emissions of free ammonia released by the production plant to practically null values and in any case to values lower than 10 ppm.

Blocks 11, 12, 13 and 14 indicate respectively a compression section of a gas flow comprising carbon dioxide, a urea synthesis section, a urea concentration section and a urea solidification section.

The compression section (block 11) comprises one or more compression stages (compressors), by means of which a gas flow comprising carbon dioxide feeding the synthesis section (block 12) is gradually compressed up to a pressure generally comprised between 100 and 450 bar.

The urea synthesis section (block 12) may be of the "oncethrough" type, i.e. without recycling of the unreacted solution, or preferably of the type with total or partial recycling to the synthesis section of unreacted ammonia and carbon dioxide.

According to the type of plant, the synthesis section may comprise one or more sequentially or parallel arranged reaction spaces which operate at a pressure generally comprised between 150 and 450 bar and at a temperature generally comprised between 160 and 215° C.

Urea is produced—in the form of an aqueous solution—in the synthesis section indicated by block 12, causing ammonia, generally in the liquid phase, and carbon dioxide in the gas phase, to react according to the following reaction:

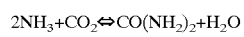

$$2NH_3 + CO_2 \Leftrightarrow CO(NH_2)_2 + H_2O$$

NH$_3$/CO$_2$ and H$_2$O/CO$_2$ molar ratios at the inlet of the synthesis section as well as the conversion yield of carbon dioxide into urea at the outlet of such section, substantially depend on the type of synthesis process utilised and may vary, for instance for NH$_3$/CO$_2$ molar ratio, from 2,5 to 4,5, for H$_2$O/CO$_2$ molar ratio, from 0,0 to 1,0, and, for the conversion yield, from 50 to 85%.

In total or partial recycle plants, the synthesis section (block 12) may also comprise a stage of decomposition (or stripping) of the solution coming from the reaction space, and a stage of condensation of the solution to be recycled to said reaction space. Generally, said decomposition and condensation stages operate at the same pressure as the reaction space.

Generally, the concentration section (block 13) comprises one or more vacuum stages that allow a concentration of the urea solution up to 99.8%, generally from 96% and 99%, obtaining therefore melt urea to be sent to the solidification section.

Generally, vacuum stages are in number of two, sequentially arranged, and comprise respective distillers that operate at a pressure comprised between 0,4 and 0,02 abar a (absolute) and at a temperature comprised between 115 and 145° C.

Generally, the melt urea solidification section (block 14) comprises a prilling section or a granulation section.

In the first case, the melt urea flow is subdivided into a plurality of small droplets that are caused to fall down as a rain in a prilling tower, in countercurrent to a "cold" air flow, which removes heat, cooling in this way urea which solidifies in a plurality of substantially spherical particles.

Alternatively, solid urea may be obtained by granulation. In this case, the melt urea flow is dispersed over a mass of growing urea granules, which are caused to move by one or more rotary drums or a fluid bed, through which an air flow is caused to pass.

Melt urea is conventionally fed to block 14 by means of suitable pumping means—not shown—located immediately downstream of block 13.

Moreover, between block 13 and block 14 the melt urea flow is generally heated by indirect heat exchange with a heating fluid, for instance steam, so as to keep urea at a temperature of over 134° C., to prevent its premature solidification.

In the absence of specific treatments, from the solidification section comes out also the free ammonia not previously separated or formed by decomposition of melt urea within the concentration section and along the path between the concentration section and the solidification section. In particular, ammonia comes out of the plant transported by the cooling air or trapped in the inside of the solid urea. The ammonia content in the air as well as in solid urea is in these cases in the order of about 50–100 ppm.

It is worth noting that ammonia trapped in solid urea evaporates in the time, polluting environment, and besides—because of bubble formation in the inside of the granules—it weakens markedly the mechanical resistance of the product, which tends to turn to powder easily.

The concentration and solidification sections are generally coupled into which is called in technical jargon finishing section of the urea plant. Between the synthesis section (block 12) and the concentration section (block 13) there is generally a urea recovery section—not shown—which provides for several recycles of the unreacted compounds to the synthesis section and allows to obtain a 60 to 85% concentrated urea solution.

The sections listed till now are those conventionally present in urea production plants, generally known to the person skilled in the art and which therefore will not be described in detail in the following of the description.

Flow line 1 represents a gas flow comprising carbon dioxide which is fed to the compression section (block 11) at a pressure generally comprised between the atmospheric pressure and 20–25 bar.

At the inlet of the urea synthesis section indicated by block 12—besides the suitably compressed gas flow comprising carbon dioxide (flow line 1)—also flow line 2, which represents an ammonia flow, preferably liquid, is let in.

The pressure and temperature of flows 1 and 2 at the inlet of the synthesis section (block 12) are those conventional for a urea plant, for instance 100–450 bar, respectively 10–200° C.

At the outlet of the synthesis section (block 12), a flow line 3 branches off which is sent to the recovery section (not shown), where urea is concentrated in steps and unreacted compounds are recycled to the synthesis section (block 12).

As a consequence, at the entry of the concentration section (block 13), flow line 3 represents a urea solution having a concentration of 60–85% and still comprising small amounts of free ammonia (in the order of 0.5–5.0% by weight).

Within the concentration section, urea is further concentrated and most of the free ammonia still present is separated and recycled to the synthesis section (block 12) through flow line 4.

Flow 3, coming from block 13 and flowing into the urea solidification section (block 14), comprises therefore melt urea together with the part of free ammonia that had not yet separated in the preceding concentration section and the ammonia formed by urea decomposition. Generally, the amount of residual free ammonia present in gas flow 3 fed to block 14 amounts to about 50–500 ppm.

In correspondence of the solidification section (block 14), besides flow line 3, also flow line 5 which represents a melt urea cooling gas—generally air at room temperature—is let in.

Solid urea obtained by prilling or granulation comes out from block 14 through flow line 6, while the cooling gas comes out through flow line 7.

In order to prevent free ammonia contained in the melt urea flow fed to the solidification section (block 14) from coming out from the plant through flow lines 6 and 7, the process according to the present invention advantageously comprises the step of feeding a gas flow comprising carbon dioxide—represented in FIG. 1 by flow line 8—to said melt urea flow (flow line 3).

Advantageously, according to the embodiment of FIG. 1, the gas flow comprising carbon dioxide is taken from flow line 1 during its passing through the compression section (block 11).

Preferably, the pressure of the gas flow comprising carbon dioxide (flow line 8) fed to the melt urea flow is comprised between 10 and 30 bar.

Particularly satisfactory results have been achieved by feeding an amount of carbon dioxide comprised between 200 and 500 $grCO_2$/tonUREA to flow line 3 comprising melt urea.

Thanks to the process according to the present invention, the emissions of residual free ammonia released by the production plant are advantageously lower than 10 ppm, therefore well under the values allowed by the anti-pollution norms in force.

By feeding excess carbon dioxide to the melt urea flow, for instance an amount comprised between 700 and 1000 $grCO_2$/tonUREA, it is even possible to eliminate entirely the ammonia released by the urea plant.

Preferably, the gas flow comprising carbon dioxide (flow line 8), is fed to the melt urea flow (flow line 3) immediately downstream of the concentration section (block 13), and more precisely immediately downstream of the means—not shown—for pumping melt urea to the solidification section (block 14).

So doing, the residence time of carbon dioxide in the melt urea flow is maximised and therefore the neutralisation of residual free ammonia is enhanced.

Moreover, thanks to the heat released by the reaction between carbon dioxide and ammonia, the operation of heating melt urea by indirect heat exchange with an external fluid can be advantageously reduced, reducing in this way also operating and energy costs.

In correspondence of said inflow of flow line 8 into flow line 3, there can be provided suitable means (not shown) for mixing carbon dioxide with melt urea, so as to facilitate the contact with free ammonia and the related neutralisation reaction.

The solid urea obtained through the present process comprises small amounts of carbamate and/or carbonates/bicarbonates, for instance comprised between 200 and 2300 kg/tonUREA which, thanks to their properties, allow to obtain a highly fertilising final product.

According to an alternative embodiment of the invention, the present process provides for the additional step of feeding the urea concentration section (block 13) with a gas flow comprising carbon dioxide, represented in FIG. 1 by the hatched flow line 9.

Also in this case, carbon dioxide comes from flow line 1 passing through the compression section (block 11). Alternatively, flow line 9, instead of directly flowing into block 13, may be inserted immediately upstream of the same, into flow line 3.

The inlet of carbon dioxide into block 13 allows for a partial neutralisation of ammonia with ensuing lightening of the work load of the vacuum stages of the concentration section, reducing therefore the amount of water to be recycled to the urea synthesis section as well as steam and energy consumption.

For this purpose, the amount of carbon dioxide fed to the urea concentration section (block 13) is preferably comprised between 6,5 and 65 $kgCO_2$/tonUREA.

The urea production plant according to this invention comprises the sections indicated by blocks 11–14 of FIG. 1.

At the inlet and between the sections that form said plant there are provided suitable feeding and respectively connection means of a type known in the art, for instance ducts, schematically represented by flow lines 1–7 of FIG. 1.

Advantageously, to reduce the emissions of residual free ammonia from the plant, the latter is provided with further means, indicated by flow line 8 in FIG. 1, to feed a gas flow comprising carbon dioxide to a melt urea gas flow coming from the concentration section (block 13).

These means may be for instance ducts or piping of a known type.

Alternatively, the plant according to the present invention includes also further means, indicated by flow line 9 in FIG. 1, to feed a gas flow comprising carbon dioxide to the concentration section (block 13).

Preferably, the above feed means are in fluid communication with flow line 1 passing through block 11, as shown in FIG. 1.

According to the present invention, a modernisation method of an existing urea production plant comprising a urea synthesis section and a urea concentration section (blocks 12 and 13), advantageously comprises the step of providing means for feeding a gas flow comprising carbon dioxide (flow line 8) to a melt urea flow coming from the concentration section (block 13).

In accordance to a further embodiment of said modernisation method according to the invention, there are advantageously provided means for feeding a gas flow comprising carbon dioxide (flow line 8) to the urea concentration section (block 13). Preferably, said feeding means are in fluid communication with means for feeding a gas flow comprising carbon dioxide to the urea synthesis section (flow line 1, block 11).

From the foregoing description emerge clearly the numerous advantages achieved by the present invention; in particular, it allows to reduce the emissions of free ammonia released by urea production plants in a simple and reliable manner, to low investment, operating and maintenance cost, providing at the same time a product having a high fertilising activity.

What is claimed is:

1. Process for reducing the residual free ammonia emissions from a urea synthesis section and a urea concentration section, characterised in that it comprises the step of:

feeding a gas flow comprising carbon dioxide into a melt urea flow coming from said urea concentration section, and reacting said carbon dioxide with free ammonia contained in the molten urea flow.

2. Process according to claim 1, characterised in that it further comprises the step of feeding a gas flow comprising carbon dioxide to said urea concentration section.

3. Process according to claim 1, characterised in that the amount of carbon dioxide fed to said melt urea flow is comprised between 85 and 850 $grCO_2$/tonUREA.

4. Process according to claim 3, characterised in that said amount is comprised between 300 and 400 $grCO_2$/tonUREA.

5. Process according to claim 2, characterised in that the amount of carbon dioxide fed to said urea concentration section is comprised between 6,5 and 65 $grCO_2$/tonUREA.

6. Process according to claim 1, characterised in that said gas flow comprising carbon dioxide is fed to the melt urea flow immediately downstream of said concentration section.

7. Process according to claim 1, characterised in that said gas flow comprising carbon dioxide is taken from a gas flow comprising carbon dioxide feeding said urea synthesis section.

8. Process according to claim 2, characterised in that said gas flow comprising carbon dioxide is taken from a gas flow comprising carbon dioxide feed id urea synthesis section.

* * * * *